United States Patent [19]

Thomas et al.

[11] Patent Number: 4,542,825
[45] Date of Patent: Sep. 24, 1985

[54] PACKAGING AND HANDLING DEVICE FOR AN ITEM THAT IS TO REMAIN PROTECTED FROM ANY DIRECT MANUAL CONTACT, AND SET INCLUDING SUCH A DEVICE AND SUCH AND ITEM

[75] Inventors: Jacques Thomas, St. Maime; Claude Raval, Dauphin, both of France

[73] Assignee: Synthese Et Creation, Forcalquier, France

[21] Appl. No.: 636,868

[22] Filed: Aug. 2, 1984

[30] Foreign Application Priority Data

Aug. 2, 1983 [FR] France ................................ 83 12717

[51] Int. Cl.⁴ .......................... B65D 85/58; B25B 3/00
[52] U.S. Cl. ..................................... 206/363; 206/349; 206/525; 206/229; 269/270; 128/303 R; 603/23
[58] Field of Search ............... 206/525, 363, 349, 229; 269/270; 128/303 R; 3/1.913, 1.912

[56] References Cited

U.S. PATENT DOCUMENTS

| | | | |
|---|---|---|---|
| 1,874,257 | 8/1930 | Doptis | 269/270 |
| 2,880,856 | 4/1959 | Albrecht | 206/205 |
| 3,150,406 | 9/1964 | Obitts | 206/5.1 |
| 4,134,157 | 1/1979 | Laure | 128/303 R |
| 4,222,382 | 9/1980 | Antonsson et al. | 128/303 R |
| 4,457,306 | 7/1984 | Borzone | 128/303 R |

Primary Examiner—William T. Dixson, Jr.
Attorney, Agent, or Firm—Becker & Becker, Inc.

[57] ABSTRACT

Packaging and handling device for an item that is to remain protected from any direct manual contact, as well as a set of such a device and such an item.

The device includes a forceps and a box cooperating in such a manner that the jaws of the forceps remain closed on the item to prevent it from any motion when the forceps are engaged in the box; this box includes a casing that is to receive the jaws of the forceps and the item and a lid towards which the forceps presents the handling means; thus, after opening of the box, the item can be accurately handled without having to take it directly in hand.

It can notably be applied to the packaging and handling of implantable prostheses.

19 Claims, 4 Drawing Figures

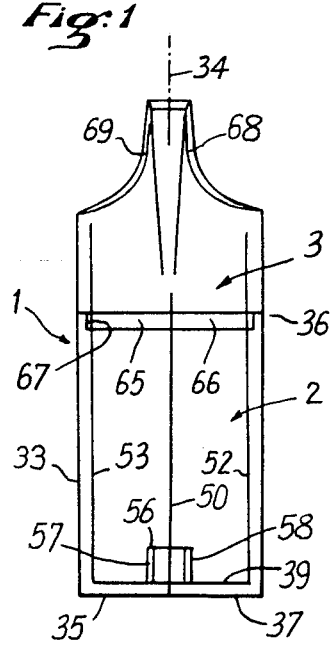
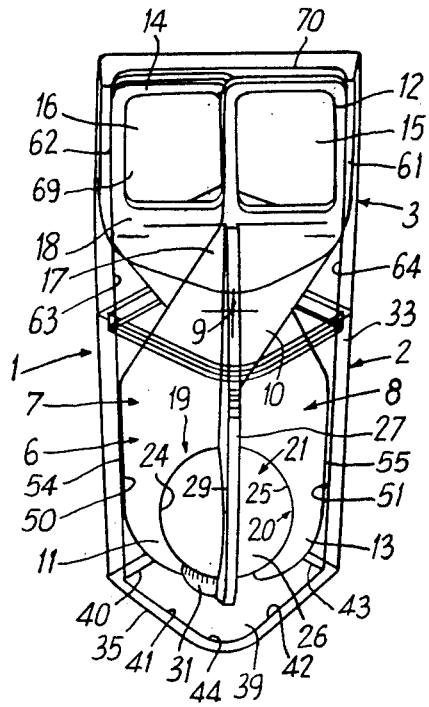
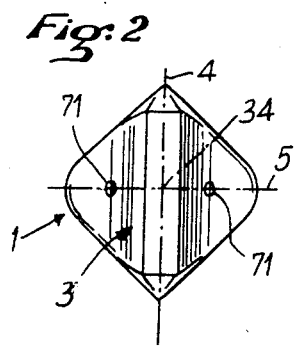
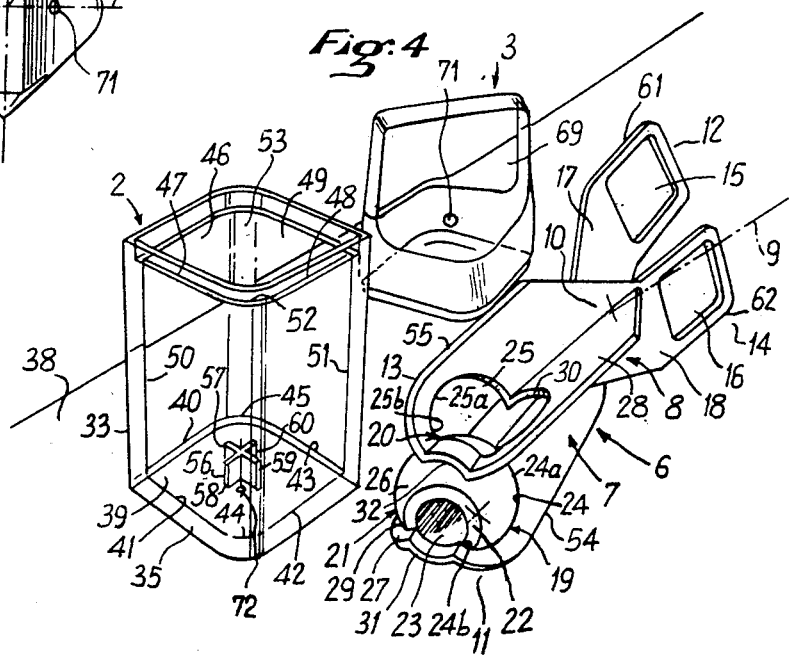

4,542,825

PACKAGING AND HANDLING DEVICE FOR AN ITEM THAT IS TO REMAIN PROTECTED FROM ANY DIRECT MANUAL CONTACT, AND SET INCLUDING SUCH A DEVICE AND SUCH AND ITEM

BACKGROUND OF THE INVENTION

The present invention concerns a packaging and handling device for an item that is to remain protected from any direct manual handling, as well as a set including such a device and such an item.

Its use may be found, among others, in the packaging and handling of implantable prostheses such as femur prosthetic heads, this being only a non limitative example.

It is known that such prostheses are packed under sterile conditions and must as much as possible be preserved under such conditions until they are implanted in the patient.

The production of packagings designed to allow the sterilization of a packed item and the preservation of this item in sterile conditions is known and for this purpose e.g. airtight bags or boxes are used.

Nevertheless the problem remains how to keep the packaged item from becoming contaminated when the packaging is being opened and pending its implantation in the patient. This problem is being solved by requiring the handling to be done by means of forceps if the person is not wearing sterile gloves.

But to remove an item from a packaging by means of forceps is not always easily done, especially if the item is in an undetermined position in the packaging, as is the case, for example, when the packaging is a bag or a sachet and if the item cannot be held easily. This inconvenience is all the more evident if the item is to be held by the foreceps in a relatively more precise position, which is the case, for example, with items which have to undergo an assembling process after they are taken out from their packaging and especially with certain types of prostheses: for example, if the considered item is a femur prosthetic head, it is necessary to assemble this head to a fastening pin, first implanted in the patient's femur, this operation being all the more difficult if one does not have a convenient grip on the femur prosthetic head of which the essentially spherical shape precisely constitutes an obstacle to a proper gripping.

It is therefore not rare that the item is directy by the hands of persons not authorized to do so, for example by an assistant not wearing sterile gloves in the case of a prosthesis, thus ruining all the precautions that have been taken previously.

The problem of avoiding a direct manual contact with a packaged item is not only to the case of sterile items, and it is possible to mention the case of items that were submitted to a treatment on their surface, such as a coating that may be damaged by the contact of the hands, as is the case for certain delicate optical or mechanical elements or certain electronic components.

The aim of the present invention is to provide a packaging and handling device overcoming the above-mentioned drawbacks.

SUMMARY OF THE INVENTION

To this end, the present invention provides a packaging and handling device for an item that is to remain protected from any direct manual contact, such as an implantable prosthesis, the device being characterized by the fact that it includes:

one forceps having at least two jaws, movable in relation to one another to evolve between a closed condition in which they are relatively close to each other so they define together a recess adapted to retain the item by a correlation of forms, and an open condition in which they are relatively apart from each other to open the said recess and thus liberate the item, the said forceps having furthermore, at a distance from the jaws, handling means which are functionally connected with the jaws to in such a way as to provide at will the open or closed condition.

a box including a casing and a lid, the said box being adaptable to receive therein the said forceps in a position in which the jaws, being closed, and the item being held in the recess formed by the jaws, are placed in the casing and the handling means are turned towards the lid.

wherein the jaws of the forceps, and the casing, have complementary forms in such a way that the casing keeps the jaws in a closed condition.

It is therefore certain that the item always keeps a perfectly determined position in relation to the forceps as long as the jaws of such forceps remain closed.

In a very simple way, the jaws of the forceps may be defined by the respective first ends of two branches which have furthermore two other ends defining the handling means, the two branches being hinged to each other in an intermediate zone located between the said first ends and the said second ends.

Other features and advantages of the device will appear from the following description in relation with the non-limiting example of such a packaging and handling device for a femur prosthetic head, as well as from the appended drawings that are an integral part of this description.

BRIEF DESCRIPTION OF THE DRAWINGS

FIGS. 1 and 2 show the closed box side view and plan view respectively.

FIG. 3 shows the cooperation of the forceps closed on the femur prosthetic head, and the box itself closed on the forceps.

FIG. 4 shows the box after it has been opened and of the forceps after it has been taken out of the box and opened.

DESCRIPTION OF PREFERRED EMBODIMENTS

On all these figures, in general 1 refers to the box which represents two planes 4 and 5 of symmetry which are perpendicular to each other; the box is formed by a casing 2 and a lid 3, both being symmetrical in relation to these two planes, the box being supposed closed as shown on FIGS. 1 and 2 for example; furthermore in general 6 refers to the forceps, formed in this example by two S-shaped identical branches 7 and 8 which are linked together on an axis 9 in a zone of mutual crossing 10 located between their two respective ends, 11 and 12 as far as branch 7 is concerned, and 13 and 14 as far as branch 8 is concerned. The linkage of branches 7 and 8 in their intermediate zone has not been detailed; any means pertaining to a man normally skilled in the Art may be used to carry out this linkage provided that it materializes the axis 9. It is possible for example, to make use for this purpose either of a supplementary part that will form a hinged joint for the two branches, or if branches 7 and 8 are made of a plastic material, a bridge of such a material, more flexible than the branches which are essentially rigid themselves but made all in one piece with the branches; the axis 9 can then be defined directly by the bridge of material or by mutual guiding means provided on the branches as it is known in itself.

The forceps 6 will now described in a more detailed manner in reference to FIGS. 3 and 4 which show them in the closed and the open condition respectively.

It is to be noted that in each of those conditions the end zones 12 and 14 are close to each other, as are the end zones 11 and 13, when the forceps are closed as shown on FIG. 3 or are spaced apart if the forceps are open as shown on FIG. 4; a relative motion of separating or bringing together which is imparted to the end zones 12 and 14 of branches 7 and 8 induces a similar motion of end zones 11 to the 13.

In order to facilitate the manual gripping of the forceps and its motion to separate or bring together the two end zones 11 and 13, each of the two end zones 12 and 14 is shaped as an eyelet designed in such a manner that it will allow the insertion of a finger of the user; this eyelet is defined as a hole, respectively 15 or 16, which passes through, follows a direction parallel to axis 9. Each end zone, defining respectively end zone 12 is formed by branch 7 or end zone 14 of branch 8, of a flat plate which along a middle plane thereof which is perpendicular to axis 9, has an S-shaped form and defines the main portion of the branch corresponding to the forceps 6; this part of the branch shaped as a plate has been referenced as 17 as far as branch 7 is concerned and 18 as far as branch 8 is concerned.

Through another end the plate 17 or 18 defines one part of the other end zone, respectively 11 or 13, of the forceps' corresponding branch and, in an intermediate zone between its own end zones, it connects tightly flat on the plate-shaped portion of the other branch to define the said zone 10 of mutual crossing and linking of the two branches 7 and 8.

In its end zone corresponding respectively to end zone 11 of branch 7 or end zone 13 of branch 8, plate 17 or 18 partially defines one jaw, respectively 12 or 20, of the corresponding branch. The two jaws 19 and 20 are placed face to face and together define a recess adapted to receive by a complementarity of form a femur prosthetic head 21 when the forceps are in a closed condition (FIG. 3); this recess on the other hand is open to free the prosthetic head 21 when the forceps is in an open condition (FIG. 4).

The shape of the prosthetic head 21 as a non limiting example, is in the general shape of a sphere having a circular flat portion 22 drilled on its center having a blind hole 23 of a general cylindrical form revolving around a radial axis with regard to the center of the sphere. In view of the fastening of the sphere on a connecting pin fitted on the patient's femur, plate 17 and 18 presents for this purpose in end zone 11 of 13 a cut-out, respectively 24 or 25, which in a plan-view is provided with a zone having the shape of an arc of a circle, respectively 24a or 25a, designed to be applied on the spherical part 26 of the outer periphery of the prosthetic head 21 following a meridian of the said part 26, and a rectilinear zone, respectively 24b or 25b, designed to be applied against the flat portion 22, following a radius of it, between the junction of this flat portion 22 with the spherical part 26 and the blind hole 23 leaving this hole completely clear.

Each of the zones 24a and 25a presents an angular development between 90° and 180° and the cut-outs 24 and 25 are set, respectively on branch 17 and plate 18, in such manner that they are facing each other and that, when the forceps are in a closed condition, the zones 24a and 25a combine to form a single circular arc of more than 180° around the spherical portion 26 of the head 21, thus preventing any movement of the head 21 parallelly with the respective middle planes of plates 17 and 18. The zones 24b and 25b of the cut-outs 24 and 25 by themselves prevent any rotation of head 21 around an axis parallel with axis 9; they constitute the respective zones of cut-outs 24 and 25 that are the farthest from axis 9 in such a way that the blind hole 23 in sphere 21 opens towards the end of forceps 6.

Furthermore, in order that the prosthetic head 21 remains held in its recess when the forceps 6 are closed, and is prevented from any movement in planes perpendicular to the respective middle planes of plates 17 and 18, those two latter parts are provided, from their intermediate zone defining the mutual crossing zone 10 to their extreme zone defining the end zone 11 or 13 of the corresponding branch 7 or 8 respectively with a lateral tab 27 or 28 respectively may advantageously be made in one piece with the corresponding plate 17 or 18.

The tab 27 is flat and presents a middle plane that includes axis 9 or is parallel with it in the immediate proximity of it, the tab being perpendicular to the middle plane of plate 17. In the end zone 11 of branch 7 the tab 27 is provided with a cut-out 29 similar to the cut-out 24 on plate 17; that is to say, the cut-out, when in plan view, has a circular arc zone designed to cover more than 90° and less than 180° of meridian of the spherical surface 26, and a rectilinear zone, farthest from axis 9, to set against the flat portion 22 between the junction thereof with the spherical surface 26 and the blind hole 23 without preventing access to this blind hole when the forceps are closed on the prosthetic head. In the same way tab 28 is provided in the end zone 13 of branch 8 with a middle plane which includes axis 9 or is parallel therewith in the vicinity thereof, and with a cut-out 30 similar in every point to cut-out 25; that is, the cut-out when in plan view, has a relatively closer zone from axis 9 with and having the form of a circular arc able to fit the surface 26 on more than 90° and less than 180°, and a zone relatively farthest from axis 9 with a rectilinear form to fit the flat portion 22 between surface 26 and the blind hole 23.

When the forceps are closed, the respective parts of the cut-outs 24, 25, 29, 30, correspond to circular arcs are disposed via a similar complementary spherical surface on surface 26 and the zones of these cut-outs which present a rectilinear plane are then coplanar, according to a plane coinciding with the plane of the flat portion 22. It will be noticed that, in order to improve the rigidity of each of the branches 7 and 8 of the forceps while improving the rest of the branches on the flat surface 22, the zone of tab 27 the farthest from axis 9, in the end zone 11 of the forceps branch 7, is connected to the corresponding part of plate 17 by means of a sector 31 presenting, towards the inside of the recess so defined as to receive the prosthetic head 21, a flat surface coplanar with zone 24b of cut-out 24 and the corresponding zone of cut-out 29. Tab 28 and plate 18 are connected in a similar way, in end zone 13 of branch 8, by means of a sector 32 presenting towards the inside of the recess for the prosthetic head 21 a surface coplanar with zone 25b of cut-out 25 and the corresponding zone of cut-out 30. When the forceps are closed, these sectors 31 and 32 allow for access to the blind hole 23 which they partially surround.

Preferably, the contact surface between cut-outs 24, 25, 29, 30 and the corresponding zones of the prosthetic head 21 are limited as much as possible. For this purpose, it is possible to give to plates 17 and 18 and to tabs 27 and 28, at the level of the respective cut-outs, the shape of ridges to assure a linear contact, and/or a shape which deviates from of strict complementarity to the form surface 26 or to the form of flat surface 22 while assuring a close precise contact with the prosthetic head 21.

Therefore the prosthetic head may be sterilized as completely as possible when it is into and immobilized in the forceps 6 which are in turn placed into and immobilized in box 1, this with the help of the complementary dispositions of this latter that are to be described now.

It appears from the figures that the casing 2 has the shape of a tubular sleeve 33 which has an axis 34 defined by the intersection of the planes of symmetry 4 and 5. The sleeve 33 is closed at one end by a flat bottom portion 35 which is perpendicular to this axis 34 while it is open at the other end 36. Preferably the sleeve 33 and its bottom portion 35 are made in one piece of a plastic material that can be sterilized.

On the casing 2 exterior, the bottom portion 35 has a flat surface perpendicular to axis 34 and on which the casing 2, possibly fitted with its lid, may rest on any horizontal surface 38 of any support. In the casing interior, this bottom portion 35 also has a planar surface 39 perpendicular to axis 34, which surface has the general shape of a square defined by four rectilinear sides 40, 41, 42, 43 parallel two by two, with the sides 40 and 41 intersecting a right angle at plane 4 and two sides 42 and 43 also intersecting each other at a right angle at plane 4. Sides 41 and 42 join one another via a curved portion 44 which crosses plane 5; and likewise, sides 40 and 43 join one another via a curved portion 45 which crosses this plane 5.

On the inside of casing 2 the tubular sleeve 33 has a peripheral cylindrical surface, generating lines of which are parallel with axis 34, and the directing line of which is constituted by the outer periphery of planar surface 39 of bottom portion 35. As a consequence the sleeve has four flat zones 46 to 49, corresponding respectively to sides 40 to 43 of surface 39. The zones 46 and 47 intersect each other at plane 4, thus defining a rectilinear ridge 50 which is parallel with axis 34. Zones 48 and 49 also intersect at plane 4 along a rectilinear ridge 41 which is parallel with axis 34. Zones 47 and 48 on the one hand and zones 46 and 49 on the other hand are connected by the rounded zones, 52 and 53 which cross plane 5, and correspond respectively to the curved portion 44 and 45 of planar surface 39 of bottom portion 35. The peripheral surface of sleeve 33 ends in the immediate proximity of opening 36, along a plane perpendicular to axis 34, and is provided around the entire periphery of opening 36 with a notch 67 remote from axis 34, the usefulness of which will be subsequently described.

It will be noticed that the tubular sleeve 33 of casing 2 has in plane 4 its largest inner dimension transversely in relation to axis 34; notably this dimension is larger than the corresponding dimension in plane 5.

Parallel with axis 34, the tubular sleeve 33 has, between surface 39 of bottom portion 35 and the opening 36, a length having the same magnitude as the distance between axis 9 and the portion of the respective end zones 11 and 13 of branches 7 and 8 which is the farthest from this axis 9. On a main portion of the respective end zones 11 and 13 of the corresponding branches, respectively 7 and 8, the plates 17 and 18 of these branches are provided along the edge opposite to the cut-outs 24, 25, that is to say towards the outside of the recess defined for the prosthetic head 21 by the jaws 19 and 20, with respective ridges 54 and 55 which are rectilinear. These hinges are parallel to each other when the forceps are in a closed condition, and are spaced apart by a distance which is less that the distance the ridges 50 and 51 but close enough that the forceps, when closed, may be introduced into casing 2 or extracted from it via the opening 36 by sliding the ridges 54 and 55 against, or practically; the ridges 50 and 51 by a relative displacement of forceps 6 and casing 2 parallel to axis 34 of the latter. The contact between ridge 54 and ridge 50 on the one hand, and ridges 55 and 51 on the other hand prevents the opening of the forceps when the end zones 11 and 13 of branches 7 and 8 of the forceps are placed into the casing 2. The ridges 54 and 55 are connected to the end section, respectively 31 or 32, of the corresponding branch via a curvilinear ridge which is, convex and, totally set back from the ridges to allow and facilitate the insertion of forceps 6, closed, into the casing 2.

It is therefore assumed that the prosthetic head 21 remains held between jaws 19 and 20, which in the end zone 11 of branch 7 and in the end zone 13 of branch 8 respectively, are provided with the cut-outs 24–29 and 25–30 respectively.

The distance which separates the ridges 54 and 55 is defined by the maximal overall dimensions of the juxtaposed end zones 11 and 13 of branches 7 and 8 of forceps 6 in a closed condition, including the prosthetic head 21 held therein. These dimensions are measured at right angles to an axis which coincides with axis 34 When the end zones 11 and 13 of the forceps are placed into the casing 2.

It should be noted that the insertion of the closed forceps into the casing 2, after rotating them 180° about axis 34, so that the ridges 54 and 55, respectively now face the ridges 51 and 50, would also be possible, but that any other way of insertion would be impossible. The inner shape of the tubular sleeve 33, compared with the distance between ridges 54 and 55 when the forceps are closed, thus avoids any erroneous insertion.

If necessary, the respective tabs 27 and 28 of branches 7 and 8 may be provided, towards the outside relative to the recess of the prosthetic head 21, with rectilinear ridges which are parallel to each other when the forceps are closed, provided that the distance separating these ridges is less than the distance separating the zones 52 and 53 in plane 5.

To improve the immobilization of the prosthetic head 21 not only in relation to the forceps 6 but also in relation to the casing 2 when, during the insertion of a closed forceps 6 holding a prosthetic head 21 into the casing 2, the prosthetic head gets close to surface 39 of the bottom portion 35 of the casing, this surface 39 is provided centrally following the axis 34, with a pyramidal protrusion 56, the shape of which may vary to a large extent. In the present example the protrusion 56 has the shape of a cross on axis 34, and is delimited away from axis 34 by means of ridges 57 to 60, which fit into the blind hole 23 of prosthetic head 21 at the end of the introduction process of the closed forceps 6 into casing 2 by means of a relative displacement parallel to axis 34.

It will be evident that the protrusion 56 may also have a different shape which nevertheless is preferably selected in such a way that during the sterilizing process the blind hole 23 may be also treated. For this purpose it will be noted that in the vicinity of the protrusion 56, and more precisely between the arms of the cross in this present example, one or more holes 72 are provided on the bottom portion 35 of casing 2 to allow for the passage of steam, these holes being open during the sterilization and then tightly closed by means of a self-adhesive tape for example.

Taking into account the dimensioning, mentioned before that the casing 2 has on its inside parallel to axis 34, the maximum insertion of the forceps 6 into the casing 2 brings the joint (which is located at the axis 9) on the level of opening 36, and the end zones 12 and 14 of branches 7 and 8, that is the eyelets defined by the holes 15 and 16, remain outside the casing 2. This considerably aids the gripping of the forceps 6.

Nevertheless, when the box is closed, the zones 12 and 14 are totally included under the lid 3 which, when placed on the casing 2, closes it in an airtight manner. Furthermore the lid 3 constitutes, advantageously, an abutment that will prevent any motion of the forceps 6, together with the prosthetic head 21 which it includes, in a direction away from the bottom portion 35 of casing 2 and along the axis 34.

Furthermore, the respective end zones 12 and 14 of branches 7 and 8, as well as the cover 3, are advantageously designed in such a manner that the placing of the lid on casing 2 tightly locks zones 12 and 14, thus helping to keep the forceps in a closed condition.

For this purpose, zones 12 and 14 are provided with rectilinear ridges, respectively 61 and 62, which are positioned parallel to and in the extension of ridges 55 and 54 respectively when the forceps are closed, thus defining the largest dimension of the forceps at the level of end zones 12 and 14, measured transversely to an axis which coincides with axis 34 when the closed forceps 6 is placed into the casing 2. The lid 3 is also provided with rectilinear parallel inner ridges, 63 and 64 which are positioned in the direct respective extensions of ridges 50 and 51 when the lid is positioned on the casing 2, so that the ridges 63 and 64 are positioned facing the ridges 62 and 61, respectively, to help prevent the opening of the forceps. It should be noted that the forceps, when closed, including the prosthetic head it holds, are totally located between ridges 61 and 55 on one hand and ridges 62 and 54 on the other hand.

A coupling between the lid 3 and the casing 2 which is compatible with such a cooperation is apparent from FIGS. 1 and 3, where it can be seen that ridges 63 and 64 extend up to an opening 65 on the lid 3. This opening is bordered with a continuous rim 66 which is adapted to fit tightly in the recess 67 which is provided in the interior of tubular sleeve 33 around the opening 36; the ridges 63 and 64 extend up to the limit of the rim 66 which is on the outside of lid 3.

In its zones adjoining opening 65, the lid 3 is provided with an inner peripheral surface extending in alignment with the one from the sleeve 33, but this inner peripheral surface narrows in a direction away from the opening 65, in such a manner that the lid 3 has in its inside, in its zone which is the farthest from the opening 65, the shape of a slot disposed along plane 4 with such dimensions that the lid encloses, in the zone, the end zones 12 and 14 of branches 7 and 8 not only by means of the ridges 61 and 62, through ridges 63 and 64, but also perpendicularly to the respective middle planes of plates 17 and 18. This zone of the lid 3 has been given the reference number 68 on the figures. It should be noted that lid 3 has a wall thickness which is practically constant. This narrowed zone 68 leads, on the outside of lid 3, to the existence of a flattened zone 69 that will considerably ease the gripping of this lid when it is placed into or taken out of casing 2.

In addition, the lid 3 is advantageously provided with openings 71 that will allow a correct sterilization. These openings are closed or sealed by any appropriate means after the sterilization process. Preferably they are arranged on the lid section that is generally parallel to the bottom portion 35 of the casing 2.

At a distance from the opening 65, the narrowed zone 68 of the inner peripheral surface of this lid ends by joining a planar surface 70 which is perpendicular to axis 34. This surface has the function of an abutment for the end zones 12 and 14 of branches 7 and 8 of forceps 6 to prevent any motion of the latter regarding a disengagement from casing 2 when the forceps are placed into it. A man normally skilled in the art will easily determine the inner dimensions given for this purpose for lid 3 by taking into account the dimensions of the forceps 6.

The mode of operation of the system that has been described may be as follows:

During the manufacturing process the prosthetic head 21 is placed, with a convenient orientation, in one of the jaws and within end zones 11 and 13 of the open forceps which are then closed for insertion into the casing 2 via the opening 36, while taking into consideration the relative angular orientation imposed, in reference to axis 34, by the inner shape of the casing 2 and the shape of the forceps. At the end of the insertion process, the prosthetic head 21 fits on the protrusion 56 on the bottom portion 35 of casing 2. It is then possible to place the lid 3 correctly in its location by aligning it with respect to the narrow zone 68. This is helped by the complementary shapes of the edge 66 and the shoulder 67 which both present inner and outer homothetic faces of the inner periphery of sleeve 33, thus preventing any possible error. The lid 3 is therefore set completely onto the casing 2 by a relative movement parallel to the axis 34. It is then possible to proceed with the sterilization process of the whole set formed by box 1, forceps 6, and the prosthetic head 21 and then blank seal the hole (or holes) such as 71 to tightly close the box 1.

During use, by gripping zone 69, a surgical assistant takes off the lid 3; this operation exposes end zones 12 and 14, by means of which the surgeon is able to directly grasp the forceps easily in his hands and use it to place the prosthetic head on the previously implanted pin. If a problem arises the surgeon is able to extract the prosthetic head in the same way and replace it in the casing 2 which remains held by the assistant, without risking contamination at any time. The perfectly rigid and sturdy shape of the forceps helps to accurately maintain the prosthetic head in a definite position, and allows the surgeon to tightly fit the prosthetic head on the pin without the direct use of his hands. The opening of the forceps liberates the prosthetic head when the final fastening has been completed.

It will be understood that, with an appropriate shape of the jaws of the forceps, the packaging device that has been described may be adapted, at will, for the handling and packaging of any prosthesis other than prosthetic femur heads and, more generally speaking, for any items that are to be protected from any direct manual handling. The mode of operation of the device may be, in all these different cases, similar to the one that has just been described but with the difference that there is no sterilization process if it is not required.

It should be noted on the other hand, that when a series of items are different from each other, but are in identical packings, that it will prove useful for a marking code to be placed on the forceps to distinguish at a glance the nature of the item. Such a code may consist of a predetermined coloration of the forceps while the casings remain translucent, for example.

The present invention is, of course, in no way restricted to the specific disclosure of the specification and drawings, but also encompasses any modifications within the scope of the appended claims.

What we claim is:

1. A packaging and handling device for an item that is to remain protected from direct manual contact comprising:
   a forceps having at least two jaws, said jaws being movable relative to one another between a closed condition in which they are relatively close to one another so that they define a recess adapted to retain the item by a correlation of shapes, and an open condition in which they are relatively apart from one another to open said recess and thus liberate the item; said forceps, at a distance from said jaws, also has handling means which are functionally connected with the jaws in such a way as to provide, at will, said open or closed condition; and
   a box which includes a casing and a lid, said box being adapted to receive therein said forceps in such a position that said jaws, when closed and holding said item in said recess formed by said jaws, are contained in said casing, and said handling means are turned towards said lid; said jaws of said forceps, and said casing, have complementary shapes, whereby said casing maintains said jaws in a closed condition.

2. A device according to claim 1, in which includes two jaws, each of which is part of a branch having a first end for receiving said item and a second end defining said handling means, the two branches being hinged together in an intermediate zone between said first ends and said second ends.

3. A device according to claim 1, wherein said lid is hollow and when said forceps are fully disposed in said casing, said handling means project beyond said casing and into said lid in a position of maximum engagement.

4. A device according to claim 1, wherein the inside of said casing and the exterior of said jaws, beyond said recess, are provided with complementary means for slidingly guiding the casing and the jaws, relative to one another along a predetermined direction when said jaws are closed, and for establishing a mutual thrust to opposite transition of said jaws into an open condition; and wherein said lid, when it closes said casing, presents thrust means to oppose any sliding of the forceps out of said casing along the aforesaid direction from its fully disposed position within said casing.

5. A device according to claim 1, wherein the inside of said casing is provided with a protrusion which is partially complementary of said item so as to immobilize said item in a fully disposed position of said forceps in said casing.

6. A device according to claim 1, wherein said box is airtight.

7. A device according to claim 5, wherein said item is capable of being sterilized.

8. A packaging and handling device for an item that is to remain protected from direct manual contact comprising:
   a forceps having at least two jaws, said jaws being relative to one another between a closed condition in which they are relatively close to one another so that they define together a recess adapted to retain the item by a correlation of shapes, and an open condition in which they are relatively apart from each other to open said recess and thus liberate the item; said forceps, at a distance from said jaws, also has handling means which are functionally connected with the jaws in such a way as to provide, at will, said open or closed condition;
   a box which includes a casing and a lid, said box being adapted to receive therein said forceps in such a position that said jaws, when closed, and holding said item in said recess formed by said jaws, are contained in said casing, and said handling means are turned towards said lid;
   said casing inside and said jaws, outside said recess, being provided with complementary means for slidingly guiding said casing and said jaws, with respect to one another, along a determinate direction when said jaws are closed, and for establishing then a mutual thrust to oppose the transition of said jaws into an open condition;
   and said lid, when it closes said casing, presents a thrust means to oppose any sliding of said forceps out of said casing along the aforesaid direction, from a position of maximum engagement of said forceps in the casing;
   said item being provided with a hole; and
   said jaws, when closed, define said recess in such a manner that it holds said item in a position such that said hole is turned away from said handling means following the aforesaid direction, and leaves this hole free; said casing is provided with a bottom portion which extends transverse to said direction and, on the inside of which, is provided with a pyramidal protrusion which is complementary of said hole and on which the hole of said item is positioned when said item is fully disposed in said casing with said handling means projecting beyond said casing and into said lid.

9. A device according to claim 8, which includes two jaws, each of which is part of a branch having a first end for receiving said item, and a second end defining handling means, the two branches being hinged together in an intermediate zone between said first ends and said second ends.

10. A device according to claim 8, wherein said lid is hollow and, when said forceps are fully disposed in said casing, said handling means project beyond said casing and into said lid.

11. A device according to claim 10, wherein said box is airtight.

12. A device according to claim 11, wherein said item is capable of being sterilized.

13. A device according to claim 12, wherein said hole on said item is capable of being assembled on a fastening pin.

14. A packaging and handling device for an item that is to remain protected from direct manual contact comprising:

a forceps having at least two jaws, said jaws being movable relative to one another between a closed condition, in which they are relatively close to one another so that they define a recess adapted to retain the item by a correlation of shapes, and an open condition in which they are relatively apart from one another to open said recess and thus liberate the item; said forceps, at a distance from said jaws, also has handling means which are functionally connected with the jaws in such a way as to provide, at will, said open or closed condition; and a box which includes a casing and a lid, said box being adapted to receive therein said forceps in such a position that said jaws, when closed and holding said item in said recess formed by said jaws, are contained in said casing, and said handling means are turned towards said lid;

each of said jaws is part of a branch having a first end for receiving said item, and a second end defining said handling means, the two branches being hinged together in an intermediate zone between said first ends and said second ends;

said lid is hollow and, when said forceps are fully disposed in said casing, said handling means project beyond said casing and into said lid;

the inside of said casing and the exterior of said jaws are provided with complementary means for slidingly guiding the casing and the jaws, relative to one another along a predetermined direction when said jaws are closed, and for establishing a mutual thrust to oppose the transition of said jaws into an open condition;

said lid, when it closes the casing, presents thrust means to oppose any sliding of the forceps out of said casing along the aforesaid direction, from its fully disposed position within said casing; and the inside of said lid and said second ends are provided with complementary means for slidingly guiding said lid and said second ends, relative to one another, along said direction when said jaws are in a closed condition; and for establishing a mutual thrust to oppose any relative motion of said second ends which could provide a transition of said jaws into a said open condition.

15. A device according to claim 14, wherein the inside of said casing is provided with a protrusion which is partially complementary of said item so as to immobilize said item when said forceps are fully disposed in said casing.

16. A device according to claim 14, wherein said item is provided with a hole; said jaws, when closed, define said recess in such a manner that it holds said item, in a position such that said hole is turned away from said handling means following the aforesaid direction, and leaves said hole free; said casing is provided with a bottom portion which extends transverse to said direction and, on the inside of which, is provided with a pyramidal protrusion which is complementary of said hole and on which the hole of said item is positioned when said forceps are fully disposed in said casing.

17. A device according to claim 14, wherein said box is airtight.

18. A device according to claim 17, wherein said item is capable of being sterilized.

19. A device according to claim 18, wherein said hole on said item is capable of being assembled on a fastening pin.

* * * * *